United States Patent [19]
Zasloff

[11] Patent Number: 5,114,921
[45] Date of Patent: May 19, 1992

[54] AMPHIPHILIC PEPTIDES AND USE THEREOF

[75] Inventor: Michael Zasloff, Merion Station, Pa.

[73] Assignee: The Children's Hospital of Philadelphia, Philadelphia, Pa.

[21] Appl. No.: 613,923

[22] Filed: Nov. 6, 1990

Related U.S. Application Data

[63] Continuation of Ser. No. 362,341, Jun. 5, 1989, abandoned, which is a continuation-in-part of Ser. No. 199,927, May 27, 1988, abandoned.

[51] Int. Cl.[5] .................. A61K 37/02; C07K 7/06; C07K 7/08
[52] U.S. Cl. ............................. 514/12; 514/13; 514/14; 514/15; 514/16; 530/324; 530/325; 530/326; 530/327; 530/328
[58] Field of Search ................ 514/12, 13, 14, 15, 514/16; 530/324-328

[56] References Cited

U.S. PATENT DOCUMENTS

| | | | |
|---|---|---|---|
| 4,107,298 | 8/1978 | Luning | 530/326 |
| 4,617,149 | 10/1986 | DiMarchi et al. | 530/324 |
| 4,636,489 | 1/1987 | Seemuller et al. | 530/324 |
| 4,659,692 | 4/1987 | Lehrer et al. | 530/324 |
| 4,668,662 | 5/1987 | Tripier | 530/324 |
| 4,791,100 | 12/1988 | Kramer et al. | 530/324 |

OTHER PUBLICATIONS

Mihara, et al, "Design and Synthesis of Basic Amphiphilic Peptides Processing Antimicrobial Activity and Their Interaction with Lipids", *Peptide Chemistry* (1985), pp. 223-228.

Lee, et al, "Effect of Amphiphilic Model Peptides on Biomembranes and Mast Cells", *Peptide Chemistry* (1985) pp. 317-320.

*Primary Examiner*—Lester L. Lee
*Attorney, Agent, or Firm*—Woodcock Washburn Kurtz Mackiewicz & Norris

[57] ABSTRACT

Amphiphilic biologically active peptides and intermediates. For example, the polypeptide comprises a chain of at least four groups of four amino acids. In each group of four amino acids, two amino acids are hydrophobic, one amino acid is basic hydrophilic, and the remaining amino acid is basic or neutral hydrophilic. A preferred amino acid sequence is Ala-Phe-Ser-Lys.

28 Claims, No Drawings

AMPHIPHILIC PEPTIDES AND USE THEREOF

This application is a continuation of Ser. No. 362,341 filed Jun. 5, 1989 and now abandoned which is a continuation-in-part of application Ser. No. 199,927, filed May 27, 1988 and now abandoned.

This invention relates to novel polypeptides. More particularly, this invention relates to novel polypeptides which are biologically active and may be used as antibiotics, antimicrobial agents, spermicides, and anti-viral agents and intermediates therefor.

Biologically active peptides called "magainins" are disclosed in *Proc. Natl. Acad. Sci.*, Vol. 84 pp. 5449-53 (Aug. '87).

In accordance with one aspect of the present invention, there is provided a synthetic polypeptide which is amphiphilic and which is positively charged (basic).

More particularly, there is provided a basic (positively charged) polypeptide having at least sixteen amino acids wherein the polypeptide includes at least eight hydrophobic amino acids and at least eight hydrophilic amino acids. Still more particularly, the hydrophobic amino acids are in groups of two adjacent amino acids, and each group of two hydrophobic amino acids is spaced from another group of two hydrophobic amino acids by at least one amino acid other than a hydrophobic amino acid (preferably at least two amino acids) and generally by no greater than four amino acids, and the amino acids between pairs of hydrophobic amino acids may or may not be hydrophilic.

The hydrophilic amino acids are generally also in groups of two adjacent amino acids in which at least one of the two amino acids is a basic hydrophilic amino acids, with such groups of two hydrophilic amino acids being spaced from each other by at least one amino acid other than a hydrophilic amino acid (preferably at least two amino acids) and generally no greater than four amino acids, and the amino acids between pairs of hydrophilic amino acids may or may not be hydrophobic.

In accordance with a particularly preferred embodiment, the polypeptide comprises a chain of at least four groups of amino acids, with each group consisting of four amino acids. Two of the four amino acids in each group are hydrophobic amino acids, and two of the four amino acids in each group are hydrophilic, with at least one of the hydrophilic amino acids in each group being a basic hydrophilic amino acid and the other being a basic or neutral hydrophilic amino acid.

The hydrophobic amino acids may be selected from the class consisting of Ala, Cys, Phe, Gly, Ile, Leu, Met, Val, Trp, and Tyr. The neutral hydrophilic amino acids may be selected from the class consisting of Ser, Asn, Gln, and Thr. The basic hydrophilic amino acids may be selected from the class consisting of Lys, Arg, and His.

Each of the groups of four amino acids may be of the sequence ABCD, BCDA, CDAB, or DABC, wherein A and B are each hydrophobic amino acids and may be the same or different, one of C or D is a basic hydrophilic amino acid, and the other of C or D is a basic or neutral hydrophilic amino acid and may be the same or different. In a preferred embodiment, the polypeptide chain may comprise 5 or 6 groups of this sequence. In each group, each of A, B, C and D may be the same in some or all of the groups or may be different in some or all of the groups.

The polypeptide chain preferably has at least 20 amino acids, and no greater than 50 amino acids. It is to be understood, however, that the polypeptide does not have to consist entirely of the groups described above. The polypeptide may have amino acids extending from either or both ends of the noted groups forming the polypeptide chain and/or there may be amino acids between one or more of the at least four groups and still remain within the scope of the invention.

The groups of amino acids may be repeating groups of amino acids, or the amino acids in the various groups may vary provided that in each group of the at least four groups of amino acids there are two hydrophobic and two hydrophilic amino acids as hereinabove noted.

Thus, in a preferred embodiment, the biologically active polypeptide comprises a chain including at least four groups of amino acids, each containing four amino acids. Two of the four amino acids in each group are hydrophobic, at least one amino acid is basic hydrophilic, and the remaining one is basic or neutral hydrophilic, with the polypeptide chain preferably having at least 20 amino acids but no greater than 50 amino acids.

In one embodiment, each of the at least four groups of amino acids which are in the peptide chain is of the sequence A-B-C-D, B-C-D-A, C-D-A-B or D-A-B-C wherein A and B are hydrophobic, one of C or D is basic hydrophilic, and the other of C or D is basic or neutral hydrophilic. The resulting polypeptide chain, therefore, may have one of the following sequences:

$(X_1)_a(A\text{-}B\text{-}C\text{-}D)_n(Y_1)$ $(X_2)(B\text{-}C\text{-}D\text{-}A)_n(Y_2)_b$ $(X_3)_a(C\text{-}D\text{-}A\text{-}B)_n(Y_3)_b$ $(X_4)_a(D\text{-}A\text{-}B\text{-}C)_n(Y_4)_b$ wherein
$X_1$ is D; C-D- or B-C-D-, $Y_1$ is -A or -A-B or -A-B-C
$X_2$ is A-, D-A- or C-D-A-
$Y_2$ is -B, -B-C or B-C-D
$X_3$ is B-, A-B-, D-A-B-
$Y_3$ is -C, -C-D, -C-D-A
$X_4$ is C-, B-C-, A-B-C-
$Y_4$ is -D, -D-A, -D-A-B
a is 0 or 1; b is 0 or 1
and n is at least 4

It is to be understood that the peptide chain may include amino acids between the hereinabove noted groups of four amino acids provided that the spacing between such groups and the charge on the amino acids does not change the characteristics of the peptide chain which provide amphiphilicity and a positive charge and do not adversely affect the folding characteristics of the chain to that which is significantly different from one in which the hereinabove noted group of four amino acids are not spaced from each other.

As representative examples of peptides in accordance with the present invention, there may be mentioned.

| I | Ala—Phe—Ser—Lys—Ala—Phe—Ser—Lys—Ala—Phe—Ser—Lys—Ala—Phe—Ser—Lys—Ala—Phe—Ser—Lys |
|---|---|
| II | Ala—Phe—Ser—Lys—Ala—Phe—Ser—Lys—Ala—Phe—Ser—Lys—Ala—Phe—Ser—Lys—Ala—Phe—Ser—Lys—Ala—Phe—Ser—Lys. |
| III | Phe—Ser—Lys—Ala—Phe—Ser—Lys—Ala—Phe—Ser—Lys—Ala—Phe—Ser—Lys—Ala— |

-continued

| | |
|---|---|
| IV | Ser—Lys—Ala—Phe—Ser—Lys—Ala—Phe—Ser—Lys—Ala—Phe—Ser—Lys—Ala—Phe—Ser—Lys—Ala—Phe— |
| V | Lys—Ala—Phe—Ser—Lys—Ala—Phe—Ser—Lys—Ala—Phe—Ser—Lys—Ala—Phe—Ser |

The peptide, may have amino acids extending from either end of the chain. For example, the chains may have a Ser-Lys sequence before the "Ala" end, and/or an Ala-Phe sequence after the "Lys" end. Other amino acid sequences may also be attached to the "Ala" and-/or the "lys" end.

Similarly, in any polypeptide chain of the present invention having at least four groups of amino acids of the sequence as described above, the chain may have, for example, a C-D sequence before the first A-B-C-D group. Also other amino acid sequences may be attached to the "A" and/or the "D" end of one of these polypeptide chains. Also there may be amino acids in the chain which space one or more groups of the hereinabove noted four amino acids from each other.

The polypeptides of the present invention are generally water-soluble to a concentration of at least 20 mg/ml at neutral pH in water. The polypeptide is non-hemolytic, i.e., it will not rupture red blood cells at effective antimicrobial concentrations. The structure of the polypeptide of the present invention provides for flexibility of the polypeptide molecule. When the polypeptide is placed in water, it does not assume an amphiphilic structure. When the polypeptide encounters an oily surface or membrane, the polypeptide chain folds upon itself into a rod like structure.

The peptides may be produced by known techniques and obtained in substantially pure form For example, the peptides may be synthesized manually or on an automatic synthesizer (J.A.C.S. Vol 85 Pages 2149-54(1963). It is also possible to produce such peptides by genetic engineering techniques.

The polypeptides of the present invention are biologically active, or bioactive. The compositions may serve as antimicrobial agents anti-viral agents, antibiotics, anti-tumor agents, spermicides, as well as exhibiting other bioactive functions.

The term "antimicrobial" as used herein means that the polypeptides of in the present invention inhibit, prevent, or destroy the growth or proliferation of microbes such as bacteria, fungi, viruses, or the like.

The term "antibiotic" as used herein means that the polypeptides employed in the present invention produce effects adverse to the normal biological functions of the cell, tissue, or organism including death or destruction and prevention of the growth or proliferation of the biological system when contacted with the polypeptides.

The term "spermicidal" as used herein means that the polypeptides employed in the present invention, inhibit, prevent, or destroy the motility of sperm.

The term "antiviral" as used herein means that the polypeptides employed in the present invention inhibit, prevent, or destroy the growth or proliferation of viruses.

The term anti-tumor as used herein means that the polypeptide inhibits the growth of or destroys tumors.

The polypeptides of the present invention have a broad range of potent antibiotic activity against a plurality of microorganisms including gram-positive and gram-negative bacteria, fungi, protozoa, and the like.

The polypeptides of the present invention allow a method for treating or controlling microbial infection caused by organisms which are sensitive to the polypeptides. Such treatment may comprise administering to a host organism or tissue susceptible to or affiliated with a microbial infection an antimicrobial amount of at least one of the polypeptides.

Because of the antibiotic properties of the polypeptides, they may also be used as preservatives or sterilants of materials susceptible to microbial contamination.

In addition, pharmaceutical compositions which comprise the polypeptides of the present invention may be combined with or placed in a non-toxic pharmaceutical carrier or vehicle such as a filler, non-toxic buffer, or physiological saline solution. Such pharmaceutical compositions may be used topically or systemically and may be in any suitable form such as a liquid, solid, semi-solid, injectable solution, tablet, ointment, lotion, paste, capsule, or the like. The polypeptide compositions may also be used in combination with adjuvants, protease inhibitors, or compatible drugs where such a combination is seen to be desirable or advantageous in controlling infection caused by harmful microorganisms including protozoa viruses, and the like.

The bioactive peptide(s) of the present invention may be administered to a host; in particular an animal, in an effective antibiotic and/or anti-tumor and/or anti-viral and/or anti-microbial and/or an antispermicidal amount.

In accordance with another aspect of the present invention, there is provided a peptide (polypeptide) having from eight to fifteen amino acids comprised of at least four hydrophobic amino acids and four hydrophilic amino acids. The hydrophobic amino acids are in groups of two adjacent amino acids wherein each group of two hydrophobic amino acids is spaced from each other by at least one amino acid other than a hydrophobic amino acid (preferably at least two amino acids) and generally no greater than four amino acids, and the amino acid(s) between pairs of hydrophobic amino acids may or may not be hydrophilic. The hydrophilic amino acids are generally also in groups of two adjacent amino acids in which at least one of the two amino acids is a basic hydrophilic amino acid and the other of the two is basic or neutral. The groups of two hydrophilic amino acids are spaced from each other by at least one amino acid other than a hydrophilic amino acid (preferably at least two amino acids) and generally no greater than 4 amino acids, and the amino acids between pairs of hydrophilic amino acids may or may not be hydrophobic.

The peptide having from 8 to 15 amino acids is amphiphilic and is positively charged (basic).

The 8 to 15 amino acid peptide hereinabove described may or may not be bioactive, and in the case where such peptide is not biactive, it has utility as an intermediate in providing the hereinabove noted peptides which have at least 16 amino acids and which are bioactive. For example, two peptides, one having eight amino acids and the other having twelve amino acids may be coupled to each other to form a peptide having 20 amino acids of the type hereinabove described and which is bioactive. The peptides may be coupled by standard peptide chemistry techniques. Thus, for example, such peptides may be condensed in solution by the technique disclosed by Johnson, et al. Peptides, pages 239-42 (Walter de Gruzter & Co., 1986).

As representative examples of such peptides, there may be mentioned peptides represented by the following structure wherein A, B, C and D are as defined previously;

$(W_1)_a(A-B-C-D)_n(Z_1)_b$     (i)

$(W_2)_a(B-C-D-A)_n(Z_2)_b$     (ii)

$(W_3)_a(C-D-A-B)_n(Z_3)_b$     (iii)

$(W_4)_a(D-A-B-C)_n(Z_4)_b$     (iv)

wherein
$W_1$ is D-, C-D-, B-C-D-
$W_2$ is A-, D-A-, C-D-A-
$W_3$ is B-, A-B-, D-A-B-
$W_4$ is C-, B-C-, A-B-C-
$Z_1$ is -A, -A-B, -A-B-C
$Z_2$ is -B, -B-C, -B-C-D
$Z_3$ is -C, -C-D, -C-D-A
$Z_4$ is -D, -D-A, -D-A-B
n is 2 or 3, a is 0 or 1 and b is 0 or 1.

The following examples are illustrative of various uses of the biologically active polypeptide compositions of the present invention. The scope of the present invention, however, is not intended to be limited thereby.

EXAMPLE

Peptide was synthesized on a 430A Applied Biosystems Synethsizer. General method utilized t-Boc chemistry of Merrifield, supra.
METHOD: t-Boc-lys (Cl-Z) - Pam Resin, substitution: 0.57 mmol/g
CHAIN ASSEMBLY: 0.5 mol scale. Preformed symmetrical anhydrides, coupled in DMF as solvent. Coupling efficiency exceeded 97% based on ninhydrin monitoring. Coupling temperatures were 10°–15° C.
CLEAVAGE: Anhydrous HF used for deblocking and removal from resin.
PURITY: greater than 95%, based on reverse phase p HLC separation, over C8 300A°, 10 cm×2.1 mm column, developed on a 0–60% Buffer B gradient in 45 min. (A=0.1% TFA; B=100% CH3CH/0.09% TFA). Visualized at 220 nm. This method is also used for peptide purification.

TABLE 1

| ANTIBACTERIAL ACTIVITY OF PEPTIDE SERIES | | |
| --- | --- | --- |
| | ZONE OF INHIBITION (mm) | |
| PEPTIDE | E. coli | S. aureus |
| 1. Ala-Phe-Ser-Lys- | 0 | 0 |
| 2. Ala-Phe-Ser-Lys-<br>Ala-Phe-Ser-Lys- | 0 | 0 |
| 3. Ala-Phe-Ser-Lys-<br>Ala-Phe-Ser-Lys-<br>Ala-Phe-Ser-Lys- | 0 | 0 |
| 4. Ala-Phe-Ser-Lys-<br>Ala-Phe-Ser-Lys-<br>Ala-Phe-Ser-Lys-<br>Ala-Phe-Ser-Lys- | 0 | 0 |
| 5. Ala-Phe-Ser-Lys-<br>Ala-Phe-Ser-Lys-<br>Ala-Phe-Ser-Lys-<br>Ala-Phe-Ser-Lys-<br>Ala-Phe-Ser-Lys- | 10 | 5 |
| 6. Ala-Phe-Ser-Lys-<br>Ala-Phe-Ser-Lys-<br>Ala-Phe-Ser-Lys-<br>Ala-Phe-Ser-Lys-<br>Ala-Phe-Ser-Lys-<br>Ala-Phe-Ser-Lys | 20 | 10 |

About $10^5$ bacteria from a mid log culture were inoculated into 8 ml of 0.7% agarose in trypticase soy broth, and layered over a plate of 1.5% agarose in trypticase soy broth. 10 ul of each peptide at a concentration of 5 mg/ml was spotted on the top layer and the plate incubated at 37° C. for 8 hrs. Zone of inhibition of growth was measured.

TABLE 2

| Antiprotozoan activity of peptides | | | |
| --- | --- | --- | --- |
| | MINIMAL DISRUPTIVE CONCENTRATION | | |
| Peptide (ug/ml) | P. caudatum | A. castellani | T. pyriformis |
| 1. Ala-Phe-Ser-Lys- | >500 | >500 | >500 |
| 2. Ala-Phe-Ser-Lys-<br>Ala-Phe-Ser-Lys- | >500 | >500 | >500 |
| 3. Ala-Phe-Ser-Lys-<br>Ala-Phe-Ser-Lys-<br>Ala-Phe-Ser-Lys- | >500 | >500 | >500 |
| 4. Ala-Phe-Ser-Lys-<br>Ala-Phe-Ser-Lys-<br>Ala-Phe-Ser-Lys-<br>Ala-Phe-Ser-Lys- | >500 | >500 | >500 |
| 5. Ala-Phe-Ser-Lys-<br>Ala-Phe-Ser-Lys-<br>Ala-Phe-Ser-Lys-<br>Ala-Phe-Ser-Lys-<br>Ala-Phe-Ser-Lys- | 50 | 10 | 50 |
| 6. Ala-Phe-Ser-Lys-<br>Ala-Phe-Ser-Lys-<br>Ala-Phe-Ser-Lys-<br>Ala-Phe-Ser-Lys-<br>Ala-Phe-Ser-Lys-<br>Ala-Phe-Ser-Lys | 10 | 5 | 10 |

About $10^2$ organisms were placed into about 200 ul of distilled water, Peptide was added from a solution of 5 mg/ml in water. The concentration at which complete physical disruption occurred within 10 minutes at room temperature as determined by direction microscopic examination is noted.

Depending on the use, a composition in accordance with the invention will contain an effective antimicrobial amount and/or an effective antispermicidal amount and/or an effective anti-viral amount and/or an effective anti-tumor amount and/or an effective antibiotic amount of one or more of the hereinabove described peptides which have such activity.

The peptides, when used in topical compositions, are generally present in an amount of at least 0.1%, by weight. In most cases, it is not necessary to employ the peptide in an amount greater than 1.0%, by weight.

In employing such compositions systemically (intramuscular, intravenous, intraperitoneal), the active peptide is present in an amount to achieve a serum level of the peptide of at least about 5 ug/ml. In general, the serum level of peptide need not exceed 500 ug/ml. Such serum levels may be achieved by incorporating the peptide in a composition to be administered systemically at a dose of about 10 mg/kg. In general, the peptide(s) need not be administered at a dose exceeding 100 mg/kg.

It is to be understood that the scope of the present invention is not intended to be limited to the specific examples described above. Various embodiments of the polypeptide compositions other than those specifically enumerated may be employed. The invention may be practiced other than as particularly described and still be within the scope of the accompanying claims.

What is claimed is:

1. A peptide containing at least eight amino acids wherein the peptide, is selected from the group consisting of the following sequences:

$(W_1)_a(A\text{-}B\text{-}C\text{-}D)_n(Z_1)_b;$ (i)

$(W_2)_a(B\text{-}C\text{-}D\text{-}A)_n(Z_2)_b;$ (ii)

$(W_3)_a(C\text{-}D\text{-}A\text{-}B)_n(Z_3)_b;$ (iii)

or $(W_4)_a(D\text{-}A\text{-}B\text{-}C)_n(Z_4)_b,$ (iv)

wherein each of A and B is a hydrophobic amino acid wherein each of A and B may be the same or different amino acids, and one of C and D is a basic hydrophilic amino acid and the other of C and D is a basic or neutral hydrophilic amino acid, and wherein:
$W_1$ is D-, C-D-, or B-C-D-;
$W_2$ is A-, D-A-, or C-D-A-;
$W_3$ is B-, A-B-, or D-A-B-;
$W_4$ is C-, B-C-, or A-B-C-;
$Z_1$ is -A, -A-B, or -A-B-C;
$Z_2$ is -B, -B-C, or B-C-D;
$Z_3$ is -C, -C-D, or -C-D-A; and
$Z_4$ is -D, -D-A, or -D-A-B, n is 2 or 3, a is 0 or 1, b is 0 or 1,
and wherein when the peptide encounters an oily surface or membrane, the peptide chain forms a rod like structure.

2. The peptide of claim 1 wherein the peptide contains at least 16 amino acids and there are at least four groups of amino acids A-B and at least 3 groups of amino acids C-D.

3. The peptide of claim 2 wherein there are at least four groups of amino acids C-D.

4. The peptide of claim 3 wherein the peptide includes at least four groups of the peptide sequence -A-B-C-D-, -B-C-D-A-, -C-D-A-B, -D-A-B-C-.

5. The polypeptide of claim 3 wherein said hydrophobic amino acids are selected from the class consisting of Ala, Phe, Gly, Ile, Leu, Met, VAl and Trp, said neutral hydrophilic amino acids are selected from the class consisting of Ser, and Thr, and said basic hydrophilic amino acids are selected from the class consisting of Lys, Arg, and His.

6. The polypeptide of claim 5 wherein at least one of said at least four groups of said four amino acids is of the sequence A-B-C-D, whrein A and B are hydrophobic amino acids, one of C is a neutral or basic hydrophilic amino acid, the other C or D is a basic hydrophilic amino acid.

7. The polypeptide of claim 3 wherein said polypeptide includes the following sequence:

-(Ala-Phe-Ser-Lys)$_4$-.

8. The polypeptide of claim 4 wherein said polypeptide comprises a chain of at least 20 amino acids and no greater than 50 amino acids.

9. The polypeptide of claim 4 wherein said polypeptide includes five groups of said sequence.

10. The polypeptide of claim 4 wherein said polypeptide includes six groups of said sequence.

11. The polypeptide of claim 1 wherein said polypeptide includes repeating groups of said four amino acids.

12. A peptide selected from the group consisting of the following sequences:

$(X_1)_a (A\text{-}B\text{-}C\text{-}D)_n(Y_1)_b$ $(X_2)_a (B\text{-}C\text{-}D\text{-}A)_n(Y_2)_b$ $(X_3)_a (C\text{-}D\text{-}A\text{-}B)_n(Y_3)_b$ or $(X_4)_a (D\text{-}A\text{-}B\text{-}C)_n(Y_4)_b,$ wherein each of A and B is a hydrophobic amino acid wherein each of A and B may be the same or different amino acids, and one of C and D is a basic hydrophilic amino acid and the other of C and D is a basic or neutral hydrophilic amino acid, and wherein:
$X_1$ is D-, C-D-, or B-C-D-;
$Y_1$ is -A, -A-B, or -A-B-C;
$X_2$ is A-, D-A-, or C-D-A-;
$Y_2$ is -B, -B-C, or -B-C-D;
$X_3$ is B-, A-B-, or D-A-B-;
$Y_3$ is -C, -C-D, or -C-D-A;
$X_4$ is C-, B-C-, or A-B-C-;
$Y_4$ is -D, -D-A, or -D-A-B;
a is 0 or 1; b is 0 or 1, and n is at least 4, and wherein when said peptide encounters an oily surface or membrane, said peptide forms a rod like structure.

13. A composition comprising:
a pharmaceutical carrier containing effective antimicrobial amount of the peptide of claim 12.

14. A composition comprising:
a pharmaceutical carrier containing effective antiviral amount of the peptide of claim 12.

15. A composition comprising:
a pharmaceutical carrier containing effective antibiotic amount of the peptide of claim 12.

16. A composition comprising:
a pharmaceutical carrier containing effective antitumor amount of the peptide of claim 3.

17. A process for inhibiting growth of a target cell or virus in a host, comprising:
administering to a host the peptide of claim 12, said peptide being administered in an amount effective to inhibit growth of a target cell or virus in a host.

18. The process of claim 17 wherein the target cell is a bacterium.

19. The process of claim 17 wherein the target cell is a fungus.

20. The process of claim 17 wherein the target cell is a tumor cell.

21. The process of claim 17 wherein the target cell is a protozoan.

22. A process for inhibiting growth of a target cell or virus, comprising:
administering to a target cell or virus the peptide of claim 12, said peptide being administered in an amount effective to inhibit growth of a target cell or virus.

23. The process of claim 22 wherein the target cell is a bacterium.

24. The process of claim 22 wherein the target cell is a fungus.

25. The process of claim 22 wherein the target cell is a tumor cell.

26. The process of claim 22 wherein the target cell is a protozoan.

27. The polypeptide of claim 12 wherein said polypeptide includes the following structure:

-(Ala-Phe-Ser-Lys)$_5$-.

28. The polypeptide of claim 12 wherein said polypeptide includes the following structure:

-(Ala-Phe-Ser-Lys)$_6$-.

* * * * *